US006296879B1

(12) United States Patent
Muscato et al.

(10) Patent No.: US 6,296,879 B1
(45) Date of Patent: Oct. 2, 2001

(54) RUMINAL FLUID INOCULATION OF CALVES

(75) Inventors: Thomas V. Muscato, Candor; James B. Russell, Ithaca, both of NY (US)

(73) Assignees: Cornell Research Foundation, Inc., Ithaca, NY (US); The United States of America as represented by the United States Department of Agriculture, Washington, DC (US)

( * ) Notice: Subject to any disclaimer, the term of this patent is extended or adjusted under 35 U.S.C. 154(b) by 0 days.

(21) Appl. No.: 09/391,775

(22) Filed: Sep. 8, 1999

(51) Int. Cl.[7] .......................... A61K 35/37; A61K 35/38; A61K 35/20
(52) U.S. Cl. ........................ 424/551; 424/550; 424/535
(58) Field of Search .................... 424/551, 550, 424/535

(56) References Cited

U.S. PATENT DOCUMENTS 4,172,127 * 10/1979 Huber .
5,785,990 * 7/1998 Langrehr .

OTHER PUBLICATIONS

Allison et al. Journal of Animal Science (1964), vol. 23, pp. 1164–1171.*

* cited by examiner

Primary Examiner—Francisco Prats
Assistant Examiner—Susan D. Coe
(74) Attorney, Agent, or Firm—Brown & Michaels, PC

(57) ABSTRACT

A method to improve the health and growth of suckling dairy calves on dairy farms includes supplementing calves' diets with a ruminal fluid preparation obtained from the rumen of a cow. This supplement provides the calves with the protection needed to develop faster and healthier. It also leads to a decreased incidence of scours in the treated calves.

13 Claims, 1 Drawing Sheet

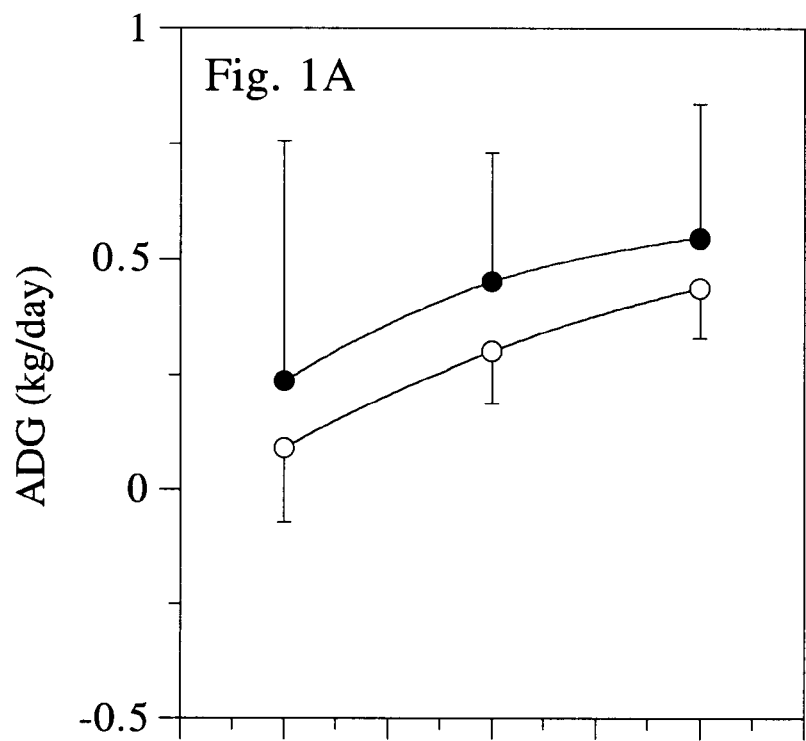
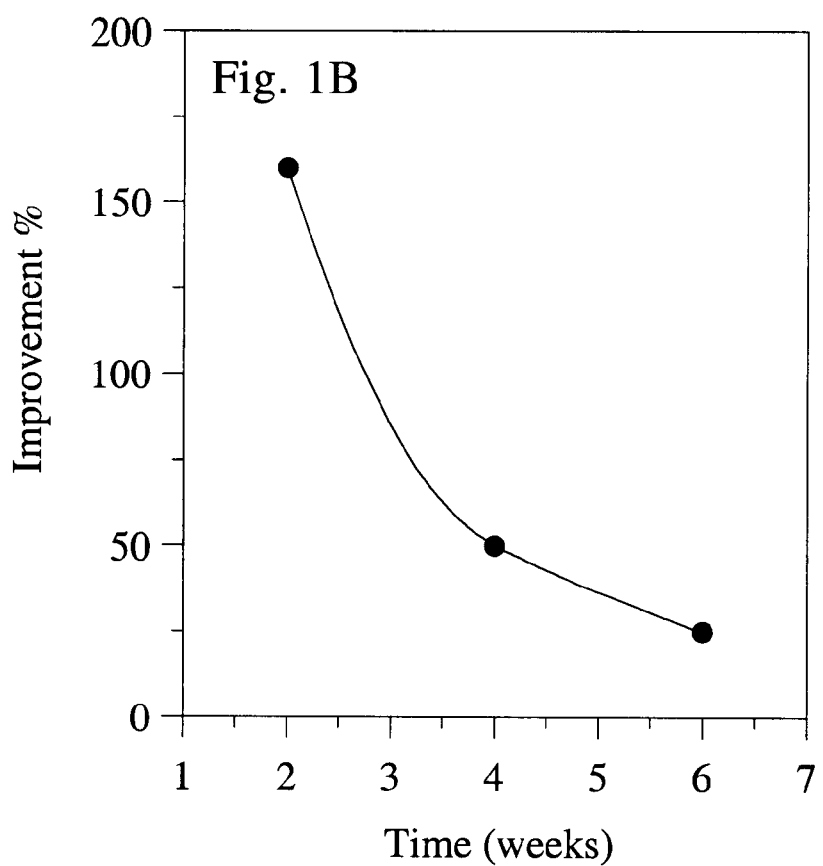

RUMINAL FLUID INOCULATION OF CALVES

ACKNOWLEDGMENT OF GOVERNMENT SUPPORT

This invention was made with Government support under Grant No. 1907-31000-002-00D, awarded by the USDA-ARS. The government has certain rights in the invention.

FIELD OF THE INVENTION

The present invention pertains to the field of dairy farming. More particularly, the invention pertains to a method of treating suckling dairy calves with ruminal fluid preparations to improve their health and growth.

BACKGROUND OF THE INVENTION

Dairy calves are subjected to an environment rich in pathogenic bacteria and microbial agents soon after birth. The calves are inherently susceptible to these agents because they are essentially born without natural immunity. As a result, infectious diseases are the main cause of calf morbidity and mortality during their first few weeks of life.

The death rate of calves can be decreased by the passive transfer of immunoglobulin from the mother cow to the new calf. This passive transfer can be achieved naturally by colostrum. Colostrum is the milk secreted for the first few days after birth and is characterized by high protein and antibody content. However, calves can only absorb antibodies soon after birth, and efforts to transfer immunity through colostrum are often unsuccessful.

At times, more than 30% (Donovan et al., "Factors influencing passive transfer of dairy calves," *J. Dairy Sci.* 69: 754–759, 1986; Norheim, et al., "An epidemiological studies of factors affecting serum IgG levels in dairy calves," *Nord. Vet.* 37: 121–135, 1985) of newborn calves do not develop immunity, or experience failure in passive transfer (McGuire et al., "Failure of colostral immunoglobulin transfer in calves dying from infectious disease," *J. Am. Vet. Med. Assoc.* 169: 713–718, 1976; McEwan et al., "Observations on the immune globulin levels of neonatal calves and their relationship to disease," *J. Comp. Pathol.* 80: 259–265, 1970; Gay et al., "Gamma globulin levels and neonatal mortality in market calves," *Vet. Rec.* 77: 148–149, 1965).

The passive immunity of new-born calves is boosted by colostrum, so the dairy industry has developed colostrum-based products that are purported to enhance the immune system. Because natural microflora protect calves from pathogens, lactic acid bacteria have been used as probiotics. Probiotics are bacteria which colonize the digestive tract and prevent colonization of pathogenic organisms.

In nature, the calf is in constant contact with the mother cow. The mother frequently licks the muzzle of the calf, and this "grooming" is a source of ruminal microorganisms. When reared on dairy farms, the calves typically are removed from the mother so that grooming is no longer possible. Calves that are taken from the mother at birth and reared in isolation lack ruminal protozoa, but these animals eventually develop a ruminal flora that contains bacteria. Ruminal fluid has never been used as a milk additive for suckling dairy calves.

An alternative to colostrum is the immunization of very young calves with conventional vaccines. However, this often fails to offer the broad protection a newborn calf needs (Selim et al., "The effect of *Escherichia coli* J5 and modified live *Salmonella dublin* vaccines in artificially reared neonatal calves," *Vaccine* 13; 381–390, 1995; Husband and Lascelles, "Antibody responses to neonatal immunization in calves," *Res. Vet. Sci.* 18: 201–207, 1975).

The sanitation and air quality of calf facilities have improved and calves are frequently isolated in "hutches" to inhibit the transmission of pathogens. However, calf health and morbidity continues to be a serious problem for the dairy cattle industry. Calves can be given low levels of antibiotics as growth promotants or larger doses as veterinary therapy, but widespread use of antibiotics in the animal industry has been criticized by the human medical field.

U.S. Pat. No. 5,785,990 to Langrehr discloses a feed fortifier and enhancer for pre-ruminant calves and a method of using the same. The inventor claims a feed fortifier containing many components. This feed fortifier results in a reduced incidence and severity of scours, a condition also studied by the present inventors as a measure of health. Generally, the patent claims that the overall health of the calves improved. However, the patent does not disclose the specific use of ruminal fluid in the feed fortifier.

U.S. Pat. No. 5,670,196 to Gregory discloses a method for microfiltration of milk or colostral whey. The invention provides a method of microfiltering milk, milk serum, colostrum, or colostral serum which provides effective bioburden reduction without substantial loss of immunoglobulins, substantially reducing the bioburden in the product while providing high immunoglobulin yields. The method makes use of charged depth filters to provide consistent bioburden control, resulting in whey products fortified with immunoglobulins.

U.S. Pat. No. 5,198,213 to Stott et al. discloses a method of disease treatment utilizing an immunologically active whey fraction. The whey is ultrafiltered through one or more different process steps to yield a filtered product having a concentration of immunologically active immunoglobulin of at least about seven percent of total solids. The filtered product is periodically tested to verify its activity to a specified microbe. The filtered product is orally administered in a therapeutically effective dose to an animal to treat a disease.

U.S. Pat. No. 4,834,974 to Stott et al. discloses an immunologically active whey fraction and recovery process. A dry, immunologically active filtered product is produced through the controlled one or two stage ultrafiltration of liquid whey containing immunologically active immunoglobulin (Ig). When fed to newborn calves, the product functions as a substitute for natural colostrum, providing both temporary passive immunity as well as initiation of the active immune system of the animal. Disease resistance and growth rate in animals, including humans, is enhanced by oral administration of the filtered product.

U.S. Pat. No. 4,816,252 to Stott et al. discloses a product and process for transferring passive immunity to newborn domestic animals using ultrafiltered whey containing immunoglobulins. Active immunoglobulins are extracted from the whey byproduct of dairy manufacturing, using ultrafiltration techniques to separate the large immuoglobulin molecules from the whey. The ultrafiltration retentate is dried to produce a filtered product having a high concentration of immunoglobulins. The dry filtered product is fed to newborn animals to transfer passive immunity. The whey-derived product is optionally used on a continuous basis as a food supplement for an animal to enable the immunologically active immunoglobulin molecules in the product to attack pathogens present in the digestive system of the animal.

U.S. Pat. No. 4,644,056 to Kothe el al. discloses a method of preparing a solution of lactic or colostric immunoglobulins or both, and use thereof, by processing milk or colostrum accompanied by precipitation of the caseins. The object of the invention is to provide a simple and economical method of preparing a solution of lactic or colostric immunoglobulins. A preferred starting material for the method in accordance with the invention is accordingly either colostrum from non-hyperimmunized mammals or human colostrum, with colostrum obtained from cows up to 30 hours after calving, with up to 5 hours after calving being particularly preferred.

Abe et al., *J Dairy Sci.* 78(12): 2838–46 (1995 Dec) disclose bifidobacteria and lactic acid bacteria. The bacteria are orally administered, resulting in an improvement in the general health of the calves receiving the bacteria. The article does not discuss or propose the use of a preparation of ruminal fluid in treatment of newborn calves.

SUMMARY OF THE INVENTION

Briefly stated, the present invention provides a method to improve the health and growth of suckling dairy calves that includes supplementing the calves' diets with a ruminal fluid preparation obtained from the rumen of a mature cow. This supplement provides the calves with the protection needed to grow faster and healthier. It also leads to a decreased incidence of scours in the treated calves.

According to one embodiment, the present invention provides a method of improving the health of dairy calves, including the steps of withdrawing ruminal fluid from the rumen of a mature cow, clarifying the ruminal fluid; and administering orally the clarified ruminal fluid to a suckling calf.

BRIEF DESCRIPTION OF THE DRAWINGS

FIG. 1A shows the average daily gain (ADG) of control calves (open symbols) and calves receiving ruminal preparations (closed symbols).

FIG. 1B shows the percent improvement due to ruminal fluid preparations.

DESCRIPTION OF THE PREFERRED EMBODIMENT

This invention utilizes a preparation of ruminal fluid to improve the health and growth of suckling dairy calves. This improvement in calf rearing allows for the extraction of a naturally occurring fluid from an adult cow. This fluid is readily available, and therefore, inexpensive. In addition, the ruminal fluid can be autoclaved to negate the risks of pathogenic organisms populating the fluid.

EXAMPLE 1

Experimental Design

Sixty dairy calves were reared under standard management conditions at the Cornell Dairy Farm. Calves were given milk twice a day, and approximately 4.0 kg of milk per day was initially provided. If calves drank all their milk and were healthy, the milk intake was increased to as much as 6.0 kg per day. A standard grain mix was provided free choice. The calves were weaned at 6 weeks of age.

Ruminal fluid administered to the calves in the groups receiving autoclaved and preserved preparations was obtained from fistulated dairy cows. Ruminal fluid administered to the calves in the group receiving fresh clarified preparations was obtained from fistulated dairy cows that were fed a diet of the standard dairy cow ration at the Cornell Dairy Farm. This ration consists of 50% grain and 50% hay. Ruminal fluid administered to the calves in the groups receiving the preserved and autoclaved preparations was obtained from another cow that was fed only hay.

The ruminal fluid was withdrawn from the bottom of the rumen using a suction device via a pipe that had holes. The pipe was ¾ inches in diameter and 30 inches long, with approximately 100 holes of ¼ inch diameter, and the end of the pope was capped with a rubber stopper. The holes in the pipe filtered the ruminal fluid so that it would not contain large feed particles.

Ruminal fluid (preserved or autoclaved) was brought to the laboratory and placed in a 39° C. water bath. Once gas production from the fermentation had buoyed residual feed particles to the top of the flask, fluid containing mixed ruminal bacteria was withdrawn from the center of the flask. Clarified ruminal fluid was mixed with preservation fluid (40% ruminal fluid and 60% preservation fluid). The preservation fluid was a glycerol salts solution that is routinely used to preserve ruminal bacteria (Teather, "Maintenance of laboratory strains of obligately anaerobic rumen bacteria," *Appl. Environ. Microbiol.* 44: 499–501, 1982; Bryant and Robinson, "Studies on the nitrogen requirements of some ruminal cellulolytic bacteria," *Appl. Microbiol.* 9: 96–103, 1962, the diclosures of which are hereby incorporated by reference). The fluid was dispensed anaerobically into glass bottles and sealed with butyl rubber stoppers. Separate batches of ruminal fluid (two liters) were heated to 121° C. for 20 minutes. Once the autoclaved ruminal fluid had cooled, it was mixed aerobically with preservation fluid as described above. Preservation fluid was also mixed with water (40% water plus 60% preservation fluid) to provide an additional control. This material was aerobically dispensed into plastic cups. All preparations were stored at −15° C. until use.

Calves were randomly assigned to five treatments with twelve calves per treatment. The first treatment was a control with no addition of fluid. In the second treatment (i.e., the additional control), the calves were presented with preservation fluid alone. The third treatment supplemented the calves' diets with fresh clarified ruminal fluid. In the fourth treatment, the ruminal fluid was preserved and frozen. The final treatment contained ruminal fluid that was autoclaved, mixed with preservation fluid and frozen. Calves were given 8 ml of each preparation per day in their milk, until weaning at 6 weeks.

Initial body weights (BW) ranged from 33.6 to 54.5 kg. The controls had a slightly lower initial body weight than the ruminal fluid treated calves, but this difference was not statistically significant (P>0.05).

All calves were weighed at 4 and 6 weeks of age. Because initial results were positive, an additional weighing at 2 weeks was implemented. However, a few calves missed this weighing. Calves were closely monitored for scours (diarrhea) and their incidence was recorded on a daily basis. If the calves appeared to be dehydrated, they were given an electrolyte solution and this administration was also recorded.

Results

When the two controls and three ruminal fluid preparations were pooled, the benefit of ruminal fluid was readily observed. Average daily gain (ADG) and percent improvement of suckling dairy calves due to administration of ruminal fluid are shown graphically in FIG. 1. Combined ruminal fluid preparations gave a statistically significant (P<0.05) increase in ADG in all three time periods. The 0 to 2 week ADG was increased 160%; the 0 to 4 week ADG was increased 50%; the 0 to 6 week ADG was increased 25%.

Initial body weight (IBW) and average daily gain of suckling dairy calves (values expressed in kg or kg per day) for each treatment are shown in Table 1.

TABLE 1

| Controls: | IBW At Birth | ADG+ 0 to 2 weeks | ADG 0 to 4 weeks | ADG 0 to 6 weeks |
|---|---|---|---|---|
| No addition[a] | 42.2 ± 4.4 | 0.07 ± 0.16 | 0.29 ± 0.11 | 0.39 ± 0.08 |
| Preservation fluid[b] | 41.6 ± 5.2 | 0.10 ± 0.17 | 0.31 ± 0.11 | 0.47 ± 0.12 |
| Ruminal preparations: | | | | |
| Fresh clarified fluid[c] | 43.4 ± 4.9 | 0.16 ± 0.19 | 0.41 ± 0.22* | 0.58 ± 0.10 |
| Preserved and frozen[d] | 43.8 ± 5.9 | 0.32 ± 0.26* | 0.51 ± 0.14* | 0.55 ± 0.16* |
| Autoclaved and frozen[e] | 44.4 ± 4.5 | 0.29 ± 0.27 | 0.42 ± 0.14* | 0.51 ± 0.15* |
| Combined Treatments: | | | | |
| Both controls | 41.7 ± 4.7 | 0.09 ± 0.16 | 0.30 ± 0.11 | 0.43 ± 0.11 |
| All ruminal fluid preps | 44.0 ± 5.0 | 0.24 ± 0.24* | 0.45 ± 0.13* | 0.55 ± 0.13* |

[a]Calves given only milk with no additions.
[b]Preservation fluid of Teather (1982).
[c]Ruminal fluid lacking large feed particles.
[d]Ruminal fluid containing mixed bacteria, preserved according to Teather (1982) and frozen at −15' C.
[e]Ruminal fluid containing mixed bacteria, autoclaved, preserved according to Teather (1982) and frozen at −15' C.
+Groups consisted of 12 calves, but on week two some of the calves were not weighed. The ADG at two weeks of control-no addition, ruminal preparation-preserved and frozen, and ruminal preparation-autoclaved and frozen only was computed with seven calves instead of 12 calves.
*Statistically different from control (P < 0.05) as indicated by Students' t-test.

Control calves with no addition of fluid performed well, and the overall average daily gain for calves from 0 to 6 weeks was 0.39 kg per day. By 4 weeks the calves in all three ruminal preparation treatment groups had a higher ADG (P<0.05) than either control (no addition or preservation fluid alone) and this difference was still evident at 6 weeks (P<0.05).

The numbers of suckling dairy calves having scours (values expressed as incidence per animal in each 2 week period) are shown in Table 2.

TABLE 2

| Controls: | Scours 0 to 2 weeks | Scours 2 to 4 weeks | Scours 4 to 6 weeks |
|---|---|---|---|
| No addition[a] | 0.92 ± 0.51 | 0.25 ± 0.45 | 0.42 ± 0.51 |
| Preservation fluid[b] | 0.50 ± 0.52 | 0.75 ± 0.62* | 0.25 ± 0.45 |
| Ruminal preparations: | | | |
| Fresh clarified fluid[c] | 0.50 ± 0.52 | 0.08 ± 0.29 | 0 ± 0* |
| Preserved and frozen[d] | 0.25 ± 0.45* | 0 ± 0 | 0 ± 0* |
| Autoclaved and frozen[e] | 0.17 ± 0.39* | 0.17 ± 0.39 | 0 ± 0* |
| Combined Treatments: | | | |
| Both controls | 0.71 ± 0.55 | 0.50 ± 0.59 | 0.33 ± 0.48 |
| All ruminal fluid preps | 0.31 ± 0.47* | 0.08 ± 0.28* | 0 ± 0* |

[a]Calves given only milk with no additions.
[b]Preservation fluid of Teather (1982).
[c]Ruminal fluid lacking large feed particles.
[d]Ruminal fluid containing mixed bacteria, preserved according to Teather (1982) and frozen at −15' C.
[e]Ruminal fluid containing mixed bacteria, autoclaved, preserved according to Teather (1982) and frozen at −15' C.
*Statistically different from control (P < 0.05) as indicated by Students' t-test.

Most of the control calves had scours while they were being fed milk. Controls receiving no addition and controls receiving preservation fluid alone had a similar incidence of scours in the 0 to 2 and 4 to 6 week periods (P>0.05), but the incidence of scours in the 2 to 4 week period was higher for preservation fluid alone than for controls receiving no addition (P<0.05).

Calves receiving ruminal preparations had a lower (P<0.05) incidence of scours than controls receiving no addition, and this effect was easily observed when the controls and ruminal fluid preparations were pooled. Ruminal fluid preparations had a lower (P<0.05) incidence of scours in all three time periods than the controls.

The numbers of suckling calves needing electrolyte therapy to prevent dehydration (values expressed as doses per animal in each 2 week period) are shown in Table 3.

TABLE 3

| Controls: | Doses 0 to 2 weeks | Doses 2 to 4 weeks | Doses 4 to 6 weeks |
|---|---|---|---|
| No addition[a] | 0.42 ± 0.51 | 0.08 ± 0.29 | 0.08 ± 0.29 |
| Preservation fluid[b] | 0.17 ± 0.39 | 0.25 ± 0.45 | 0.08 ± 0.29 |
| Ruminal preparations: | | | |
| Fresh clarified fluid[c] | 0 ± 0 | 0 ± 0 | 0 ± 0 |
| Preserved and frozen[d] | 0.08 ± 0.29 | 0 ± 0 | 0 ± 0 |
| Autoclaved and frozen[e] | 0 ± 0 | 0 ± 0 | 0 ± 0 |
| Combined Treatments: | | | |
| Both controls | 0.29 ± 0.46 | 0.17 ± 0.38 | 0.08 ± 0.28 |
| All ruminal fluid preps | 0.03 ± 0.17* | 0 ± 0* | 0 ± 0 |

[a]Calves given only milk with no additions.
[b]Preservation fluid of Teather (1982).
[c]Ruminal fluid lacking large feed particles.
[d]Ruminal fluid containing mixed bacteria, preserved according to Teather (1982) and frozen at −15' C.
[e]Ruminal fluid containing mixed bacteria, autoclaved, preserved according to Teather (1982) and frozen at −15' C.
*Statistically different from control (P < 0.05) as indicated by Students' t-test.

Controls often needed electrolyte therapy while they were consuming milk. Fewer electrolyte treatments were provided to calves given ruminal fluid preparations than controls receiving no addition. When the controls and ruminal fluid preparations were pooled, statistically significant decreases in electrolytes were noted in the 0 to 2 week and 2 to 4 week periods.

The cumulative average daily milk intake (ADMI) of suckling dairy calves (values expressed as kg per day) is shown in Table 4.

TABLE 4

| Controls: | ADMI 0 to 2 weeks | ADMI 0 to 4 weeks | ADMI 0 to 6 weeks |
|---|---|---|---|
| No addition[a] | 4.50 ± 0.46 | 4.55 ± 0.59 | 4.63 ± 0.60 |
| Preservation fluid[b] | 4.43 ± 0.39 | 4.73 ± 0.62 | 4.81 ± 0.64 |
| Ruminal preparations: | | | |
| Fresh clarified fluid[c] | 4.39 ± 0.52 | 4.53 ± 0.61 | 4.51 ± 0.62 |
| Preserved and frozen[d] | 4.97 ± 0.26 | 5.20 0.30* | 5.23 0.35* |
| Autoclaved and frozen[e] | 4.58 ± 0.57 | 4.66 0.63 | 4.68 0.61 |
| Combined Treatments: | | | |
| Both controls | 4.47 ± 0.42 | 4.64 0.60 | 4.72 0.62 |
| All ruminal fluid preps | 4.65 ± 0.52 | 4.80 0.60 | 4.81 0.61 |

[a] Calves given only milk with no additions.
[b] Preservation fluid of Teather (1982).
[c] Ruminal fluid lacking large feed particles.
[d] Ruminal fluid containing mixed bacteria, preserved according to Teather (1982) and frozen at −15' C.
[e] Ruminal fluid containing mixed bacteria, autoclaved, preserved according to Teather (1982) and frozen at −15' C.
*Statistically different from control (P < 0.05) as indicated by Students' t-test.

Calves receiving fresh and autoclaved ruminal fluid preparations received the same amount of milk as controls receiving no additions (P>0.05), but calves receiving frozen ruminal fluid preparation received more milk than controls with no addition (P<0.05). When the controls and ruminal fluid preparations were pooled, however, the average daily milk intake was not statistically different (P>0.05).

The calves in this study received whole milk containing no added antibiotics. It is expected that the benefits of administering ruminal fluid would be even greater for calves being fed milk replacer.

Interpretation of Results

The results indicated that calves receiving ruminal fluid preparations were healthier and had a higher average daily gain (ADG) than calves that did not receive any addition or only the preservation fluid. Because the amount of ruminal fluid administered was relatively small (8 ml per day), it is unlikely that the ruminal fluid was simply providing nutrients.

The decrease in scours and electrolyte therapy indicated that ruminal fluid preparations were improving animal health. Probiotics are thought to displace pathogenic bacteria from the gastrointestinal tract, and we had originally thought the ruminal fluid preparations might act in this fashion. The observation that autoclaved ruminal fluid preparations had approximately the same activity as a fresh or preserved fluid indicated that the ruminal fluid preparations were not acting as a probiotic per se.

The observation that the autoclaved ruminal fluid preparation retained its activity also has practical advantages. Ruminal microorganisms can be preserved with glycerol and salts, but there is gradual decrease in viable cell numbers. Ruminal fluid does not usually contain large numbers of pathogenic organisms, but there is always a possibility that pathogens (e.g., Salmonella and E. coli) could be transferred to the calf via fresh or preserved preparations. The autoclaved ruminal fluid preparation would be free of potential pathogens. Furthermore, the fact that the protective action of the ruminal fluid is retained after autoclaving indicates that the product should also retain this feature even after drying, such as by lyophilization or freeze-drying.

Since it is a well documented fact that proteins can act as antigens and stimulate the immune system, the ruminal fluid preparations would have contained a variety of proteins (derived from ruminal microorganisms and feed consumed by the donor cow). Any of these proteins could act as potential antigens.

The mechanism of ruminal fluid preparations in stimulating the growth and health of dairy calves has not yet been determined, but a phenomenon known as "immunotolerance" could be involved. When potential antigens reach immature lymphoid cells during neonatal development, these antigens can suppress future responses to that antigen. Immunotolerance can be induced in the adult as well as the neonate, but a much higher dose of antigen is required. If proteins from autoclaved ruminal fluid preparations allowed the calves to suppress antibody production against normal non-harmful gut bacteria, it is conceivable that the calf could have a greater antigenic (antibody) response against pathogenic bacteria that cause scours (diarrhea).

Further work is needed to more precisely define the time and amount of ruminal fluid preparation that is needed, but these experiments are relatively straightforward. Calves could be given the ruminal fluid preparation immediately after birth and these calves could be compared to those receiving a sustained daily dose (8 ml per day for 6 weeks). If the ruminal fluid preparations are only needed immediately after birth, the value of preparations as a commercial product would be enhanced. The 8 ml daily dose was an arbitrary amount, and calves receiving smaller amounts could be compared to those receiving 8 ml or possibly even more. If the amount of ruminal fluid preparation can be reduced, the commercial value would be enhanced.

The particular rumen microorganisms contained in ruminal fluid preparations that are responsible for stimulating the growth and health of dairy calves have not yet been determined, but it should be relatively straightforward to identify the particular species that elicit the response, using the techniques that are well known to those of ordinary skill in the art. Once such species are identified, they can be isolated and cultured using standard microbiological techniques and administered directly in pure form or mixed with other components.

Similarly, it should be relatively straightforward to identify the particular proteins produced by the species that elicit this response, using the techniques that are well known to those of ordinary skill in the art. Once such proteins are identified, they can be isolated and cloned, using the standard techniques of molecular biology and administered directly in pure form or mixed with other components.

Further, either fresh or autoclaved ruminal fluid itself, ruminal fluid mixed with preservation fluid or other components, the particular microorganisms or the particular proteins or fragments thereof can be dried or freeze-dried, using drying techniques that are well known in the art, and administered in powder or tablet form, or mixed with feeds in a dried form.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

What is claimed is:

1. A method of improving the health of a dairy calf, comprising the steps of:
    a) withdrawing ruminal fluid from the rumen of a mature cow;
    b) sterilizing said ruminal fluid; and
    c) administering orally said sterile ruminal fluid to a suckling calf.

2. The method of claim 1, wherein said ruminal fluid is clarified prior to administering to said calf.

3. The method of claim 1, wherein said ruminal fluid is frozen.

4. The method of claim 1, wherein said ruminal fluid is dried.

5. The method of claim 1, wherein said ruminal fluid is administered one or more times per day in an effective amount consisting essentially of about 8 milliliters or less.

6. The method of claim 1, wherein said ruminal fluid is administered twice per day for a duration of about 6 weeks.

7. The method of claim 1, wherein the average daily weight gain of said calf is increased.

8. The method of claim 1, wherein the incidence of scours in said calf is decreased.

9. The method of claim 1, wherein said ruminal fluid is mixed with a preservation fluid.

10. The method of claim 9, wherein said preservation fluid comprises a glycerol salt solution routinely used to preserve rumen bacteria.

11. The method of claim 9, wherein said ruminal fluid mixture is frozen.

12. A method of improving the health of an immature animal, comprising the steps of:
    a) withdrawing gastrointestinal fluid from a mature animal;
    b) sterilizing said gastrointestinal fluid; and
    c) administering orally said sterile gastrointestinal fluid to an immature animal.

13. A method of improving the health of a dairy calf, comprising the steps of:
 a) withdrawing gastrointestinal fluid from a mature animal;
 b) sterilizing said gastrointestinal fluid; and
 c) administering orally to an immature animal a composition selected from the group consisting of:
  i. said sterile gastrointestinal fluid;
  ii. a composition derived from said sterile gastrointestinal fluid;
  iii. a non-viable organism derived from said sterile gastrointestinal fluid; and
  iv. a protein derived from said organism.

\* \* \* \* \*